United States Patent
Rothenfusser et al.

(10) Patent No.: US 7,822,268 B2
(45) Date of Patent: Oct. 26, 2010

(54) ADVANCED PROCESSING OF ACTIVE THERMOGRAPHY SIGNALS

(75) Inventors: Max Rothenfusser, Munich (DE); Robert E. Shannon, Oviedo, FL (US); Matthias Goldammer, Munich (DE); Christian Homma, Vaterstetten (DE)

(73) Assignee: Siemens Energy, Inc., Orlando, FL (US)

( * ) Notice: Subject to any disclaimer, the term of this patent is extended or adjusted under 35 U.S.C. 154(b) by 1177 days.

(21) Appl. No.: 11/447,731

(22) Filed: Jun. 6, 2006

(65) Prior Publication Data

US 2007/0288177 A1    Dec. 13, 2007

(51) Int. Cl.
    *G06K 9/00*      (2006.01)
(52) U.S. Cl. ........................ 382/162; 382/141
(58) Field of Classification Search ......... 382/162–167, 382/141–152; 250/330, 332, 339.02, 339.14, 250/341.1, 341.6, 358.1; 356/51; 374/5, 374/7, 10, 120, 121, 124, 137; 209/577; 348/86, 125; 700/95, 212; 358/1.9, 518; 345/22, 589; 702/130, 135–136
See application file for complete search history.

(56) References Cited

U.S. PATENT DOCUMENTS

| | | | |
|---|---|---|---|
| 6,057,931 A * | 5/2000 | McConnell et al. ......... 358/1.9 |
| 6,367,969 B1 * | 4/2002 | Ringermacher et al. ........ 374/7 |
| 6,516,084 B2 | 2/2003 | Shepard |
| 6,751,342 B2 | 6/2004 | Shepard |
| 7,186,981 B2 * | 3/2007 | Shepard et al. .......... 250/341.1 |
| 7,454,050 B2 * | 11/2008 | Garvey ........................ 382/141 |
| 7,591,583 B2 * | 9/2009 | Foes et al. ...................... 374/5 |
| 2002/0044679 A1 | 4/2002 | Shepard |
| 2002/0172410 A1 | 11/2002 | Shepard |
| 2003/0193987 A1 | 10/2003 | Zalameda |
| 2004/0217289 A1 | 11/2004 | Raulerson et al. |
| 2005/0008215 A1 | 1/2005 | Shepard |

OTHER PUBLICATIONS

Takahide Sakagami, Shiro Kubo, Takeshi Endo and Yoshifumi Asakura; "Development of a new processing technique of sequential temperature data after pulse heating for quantitative nondestructive testing"; Thermosense XXVI; Proc of SPIE—The International Society for Optical Engineeing SPIE-INT.; vol. 5405, No. 1; 2004; pp. 357-365; XP-002461748; ISSN: 0277-786X.

* cited by examiner

*Primary Examiner*—Sherali Ishrat

(57) ABSTRACT

A method for processing thermography signals. A time series of radiometric data is measured from a surface (104) of an object (102) over a period of heating and subsequent cooling, and a mathematical curve (1, 2) is fit to the data. An amplitude aspect and one or more shape aspects are identified for each curve. The amplitude and shape aspects are then used together to characterize features such as defects in the object. The amplitude and shape aspects for an array of such data may be combined in a single noise-free visual display (100) by associating hue (color) with the shape aspect and luminance (brightness) with the amplitude aspect. Optionally, a second shape aspect may be identified and associated with saturation on the display. A visible image of the object may be overlaid on the display.

12 Claims, 5 Drawing Sheets

ADVANCED PROCESSING OF ACTIVE THERMOGRAPHY SIGNALS

FIELD OF THE INVENTION

This invention relates to processing, analysis, and display of a thermographic time series of an object during and after energizing the object in a contact or non-contact process for analysis, especially for defect detection.

BACKGROUND OF THE INVENTION

Active thermography is a non-destructive evaluation (NDE) technique in which energy with a certain time and/or spatial structure is applied to a test object, and a resulting temperature distribution on a surface of the object is measured with an infrared camera. From the recorded infrared sequence, information about defects, surface structure and the inner structure of the object may be obtained. The image is digitized into picture elements, or pixels, each representing a small unit area on the test object surface. The temperature/time signal is processed and evaluated per pixel and in patterns of pixels.

In active thermography, energy may be applied to a test object by electromagnetic induction, mechanical vibrations including ultrasound, flash radiation, laser, hot air, or microwave excitation. In a pulsed version of active thermography, the excitation power is switched on for a time period of typically 1 millisecond to over 1.5 seconds, depending upon the application.

BRIEF DESCRIPTION OF THE DRAWINGS

The invention is explained in following description in view of the drawings that show.

DETAILED DESCRIPTION OF THE INVENTION

Figure 1:
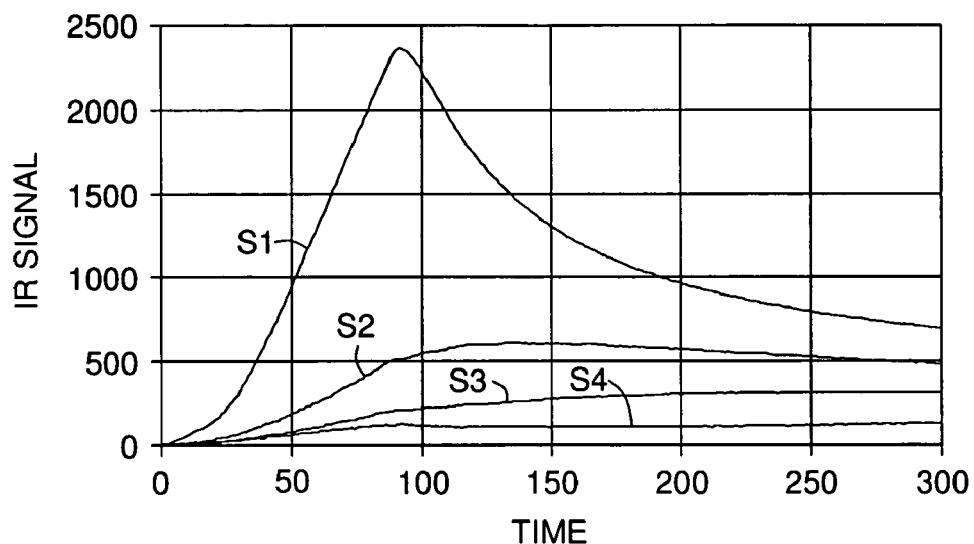
FIG. 1 various temperature/time signals from induction thermography.
Figure 2:
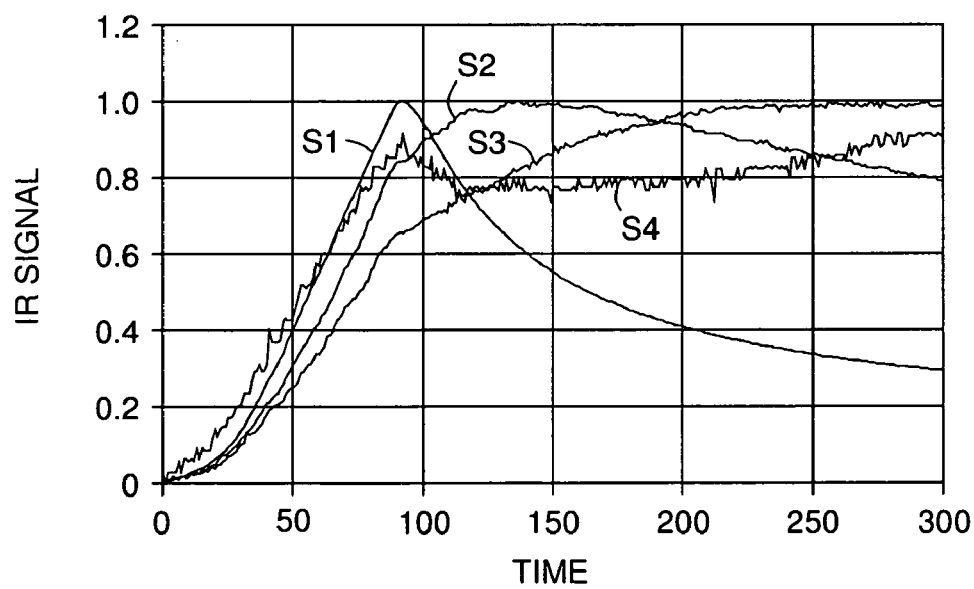
FIG. 2 normalized temperature signals.

FIG. 1 illustrates examples of typical infrared (IR) detector output/time signal curves S1-S4 produced during a thermographic inspection conducted in accordance with the present invention. These curves are typical of an individual IR detector element. An IR image, or thermogram, consists of a two-dimensional array of such individual elements. The IR detector output is related to photon intensity, which is a function of the object temperature, object emissivity, and the travel path of the photon from the object to the image array through the environment and system optics. At time zero the temperature rise is zero, relative to an unheated starting temperature. The thermal signal increases as energy is applied to the test object during an energizing phase, reaches a maximum at some point, then decreases during a non-energizing phase once the energy is no longer being applied to the test object. The point of peak temperature production is related to the cutoff of energy application, but depending upon the location of the point of measurement relative to other structures in the test object, detection of the peak temperature change may be somewhat after the energizing cutoff time due to thermal lag and heat conduction through the part. One immediately noticeable difference among these curves is their amplitudes. FIG. 2 shows the curves S1-S4 normalized to each curve maximum, which more clearly reveals differences in their shapes. (note that the peak IR signal value of 1.0 for curve S4 occurs at a time of about 350 ms and thus is not visible in the figure) For example, differences in the times of the maxima and in the slopes of the heating (energizing) and post-heating (non-energizing) phases can be seen. The shapes of the curves correspond to both the defect geometry and the geometry and material properties of its surroundings within the part/sample being inspected. Therefore, the present invention exploits techniques that enhance the "contrast" between these curves in order to better differentiate between defective zones and intact areas.

Figure 3:
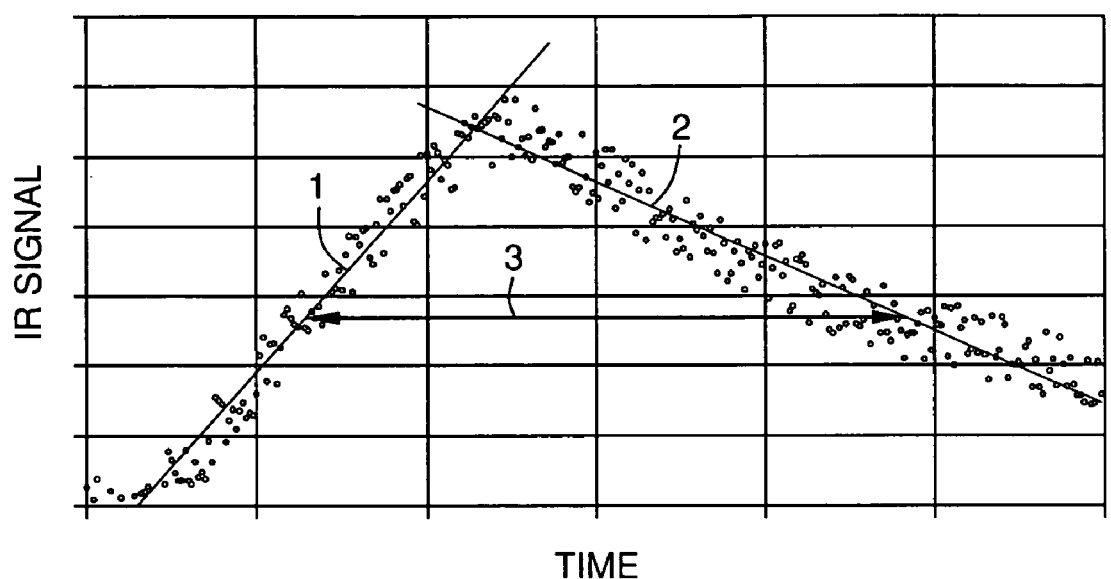
FIG. 3 thermographic data fitted with linear functions.
Figure 4:
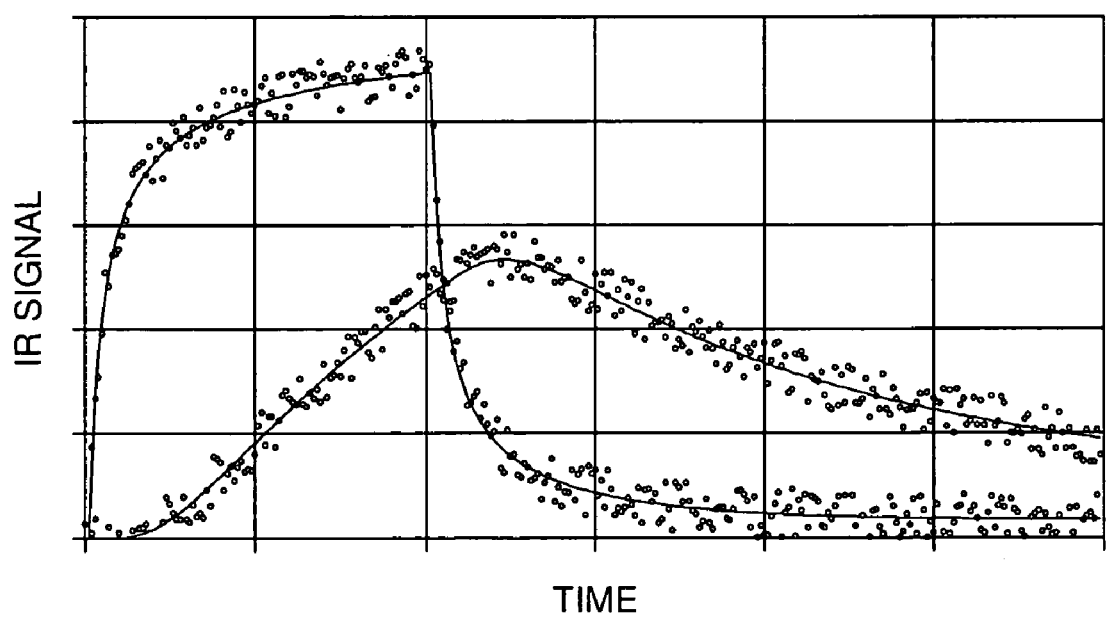
FIG. 4 thermographic data fitted with error functions.

Various methods can be used to extract information about the amplitude and shape of such temperature signals. For example, straight lines 1, 2 can be fitted to the two phases (heat up and post-heating) of the signal data, as shown in FIG. 3. The amplitude maximum is then defined by the intersection of the two lines 1, 2. The slope of each line 1, 2 provides information about the signal shape, which corresponds to the defect and the sample geometry. In linear equation 1 below, the parameters T, t, a, and b respectively represent temperature, time and the fit parameters (a and b) for the individual lines 1, 2.

$$T(t) = a + (b \cdot t) \tag{1}$$

An advantage of a linear fit is the fast and simple calculation of the coefficients.

Instead of a straight line, an exponential curve such as represented by equation 2 may be fit to the thermal data in the post-heating phase. For a number of heating methods, the temperature decay in the cool-down phase approximately follows an exponential function, which can be parameterized with an exponential fit.

$$T(t) = a \cdot \exp(b \cdot t) \tag{2}$$

Another type of fitting function that can be used is a polynomial function of the order n.

$$T(t) = a_0 + a_1 \cdot t + a_2 \cdot t^2 \ldots + a_n \cdot t^n \tag{3}$$

These functions may be more precise than equations 1 and 2 in their accuracy of fit, depending upon the number of fit parameters. Separate functions may be used for the heat up and the post-heating phases. Such separate curves may be constrained to intersect at a predefined time, such as the excitation cutoff time, by a constraint in the fitting algorithm using known mathematical techniques.

Depending on the order of the polynomial, a differing number of fit parameters is obtained. The most significant ones may be determined according to the excitation technique, specimen and location of the defect. In addition, combinations of the fit parameters may be used, such as weighted sum or any other mathematical combination that correlates to the defect. In U.S. Pat. No. 6,516,084 a method is described that enhances the visibility of defects by smoothing the data and by further processing of the temperature development over time by using a polynomial fit to preprocess the data from the infrared camera. In contrast, one embodiment of the present invention uses the resulting polynomial fit parameters directly and visualizes them in an image.

In acoustic thermography, defects such as cracks generate heat because the test object is caused to vibrate by an application of acoustic energy, and heat from friction, elastic deformation and plastic work is produced at the crack. Usually the defect-free areas do not show a significant temperature rise. In ideal thermal models of homogeneous materials, the temperature/time signals of heat sources, including point, line, or area sources, can be expressed by analytical functions based on the so-called error functions (equation 4).

$$\mathrm{Erf}(t) := \frac{2}{\sqrt{\pi}} \int_0^t e^{-s^2} ds \qquad (4)$$

Equation 5, for example, describes the temperature field for a point heat source at a depth $z_0$ in a homogeneous material, where the point source is heated for a time period $\tau$. The parameters Q and $\alpha$ represent the amount of heat generated and the thermal diffusivity, respectively.

$$T(t, x, y, z) = \frac{Q}{4\pi\alpha\tau\sqrt{x^2 + y^2 + z^2}} \left( 1 - \mathrm{Erf}\sqrt{\frac{x^2 + y^2 + (z - z_0)^2}{4\alpha t}} \right) \qquad (5)$$

When using these types of functions for the fitting procedure, only the time dependency need be taken into account, because for each pixel the position (x,y,z) is constant. Error-function based waveforms are useful for (but not limited to) acoustic thermography, since usually, no heating in addition to that generated in the defect zone is apparent. Thus the physical model used for deriving equations (4) and (5) can be fully used. Other techniques may apply additional heating that disturbs the model if not accounted for.

Curve-fitting procedures require many individual values of functions to be calculated. This computation-intensive process can be optimized by pre-calculating a set of solutions for a function and storing them in a table, which is then used for lookup by function variable(s) such as time, as known in computer science. This method can speed the fitting process substantially. Such tabulation of functions is generally advantageous for types of curve fitting where iterative algorithms are used (non-linear fits) or where complicated functions are involved.

Figure 5:
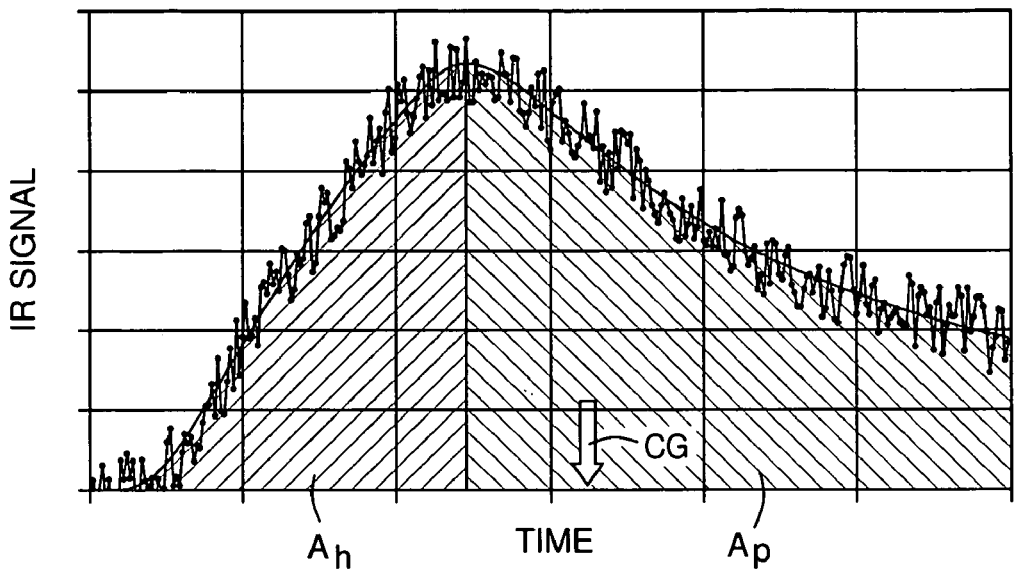
FIG. 5 signal shape aspects—areas and center of gravity.

As shown in FIG. 5, the areas $A_h$ and $A_p$ under the curves of the heating and post-heating phases, respectively, provide information about the signal and the related defect, and can be used to differentiate temperature signals and thereby to diagnosis a type of defect or other structure causing the signal. A measure for the total heat energy emitted during a given time interval, for example, is given by equation 6.

$$T\_\mathrm{integral} = A_h + A_p \qquad (6)$$

Equations 7 and 8 are examples of formulas based on areas $A_h$ and $A_p$ under the curves that provide parameters for describing the signal shape. Any modification of these formulas may be considered, for example, the application of square, cube, square root, and other functions to $A_h$ and $A_p$ or combinations of them.

$$\text{Parameter 1} = (A_p - A_h)/(A_p + A_h) \qquad (7)$$

$$\text{Parameter 2} = A_p/A_h \qquad (8)$$

The calculated area is especially useful if the total energy deposited at the site of the defect in the form of heat is to be visualized.

For fast differentiation of the shapes of temperature signals, a center of gravity equation of the areas underneath the curves of both phases may be used as in equation 9. For a fast decay in the post-heating phase, for example, the center of gravity is close to the beginning of this phase; however, for a slow decay it is shifted toward the end of this phase. This center of gravity parameter also resolves a potential delay of the temperature maximum, which is usually due to the time the heat needs to diffuse to the viewed position, and therefore correlates with the depth of the defect within the material, or with a lateral distance between the heat-generating defect and the point of temperature detection, and may be used as an estimation of the defect position. The time range used for the calculation of the integral can be adapted to the individual application.

$$\text{Parameter 3} = \mathrm{Integral}\{T(t) \cdot t \cdot dt\}/\mathrm{Integral}\{T(t)dt\} \qquad (9)$$

A Fourier transform, which is based on sinusoidal functions, may be applied to the measured data. However, there are other orthogonal functional systems that may be used instead. Examples include Hermite polynomials, Laguerre functions, Spherical Bessel functions, and Legendre polynomials.

Some functions fit certain signal shapes better than others, and signal shapes in turn depend on factors such as the excitation method and duration, the structure type and material, and the defect type and its location in the structure, especially its depth. The present inventors find certain functions to be used advantageously for curve fitting for the respective method of heating shown in Table 1.

TABLE 1

| | Technique | | | | |
|---|---|---|---|---|---|
| | Flash | Hot-air | Laser | Ultrasound | Induction |
| Linear | | | X | | X |
| Exponential | | | X | | X |
| Polynomial | X | X | X | X | |
| Error functions | | | | X | |
| Area | | | | | X |
| Center of gravity | | | | | X |
| Orthogonal set | | X | | X | X |
| Synthetic functions | X | | | X | X |

Instead of using analytically defined functions, synthetic waveforms may be used for the fit. The data of the selected function are stored in a table and used for the fit procedure using the tabulation optimization method mentioned previously. An advantage of synthetic functions is that they can be defined as close as possible to typical temperature signals in a given test situation.

Selection of the best function for analyzing a given thermal signal area can be done automatically if sufficient computing power is available. This process lends itself to parallel computing, in which the curve-fitting task can be performed with each function simultaneously on different processors, as known in computer science. The results may then be compared, and the function with the best fit may be selected as known in mathematics.

Once the curve fitting is completed, a shape aspect of the curve(s) may be derived from at least one calculation related to the curve. First, the type of function selected as providing the best fit to the data is, itself, a shape aspect that may be responsive to the type of defect or feature radiating heat in a given area. Other examples of identifying a shape aspect include calculating an average slope of the curve during the energizing phase, an average slope of the curve during the non-energizing phase, a time associated with a delay of a curve maximum with respect to an energizing cutoff time, a center of gravity of the area integrated under the curve over the time period, a ratio of an area under the curve before a maximum of the curve to an area under the curve after the maximum of the curve, and a ratio of an area under the curve during the energizing phase to an area under the curve during the non-energizing phase. A further shape aspect is represented by the time period defined by a length of a line drawn between the energizing phase and the non-energizing phase curves at a specified amplitude (such as at a specified percentage of the peak amplitude), such as illustrated by line 3 in FIG. 3. Such a time period may be divided into its energizing portion and its non-energizing portion and a further shape aspect may be expressed as a ratio of the time period above a predetermined amplitude during the energizing phase and the time period above that same predetermined amplitude during the non-energizing phase. Alternatively, the ratio of the peak amplitude and the length of line 3 may represent a shape aspect.

Conventionally a grey level for each picture element or pixel corresponds to a level of a single parameter at a corresponding unit area on the object at a single time. The image may be displayed in pseudo colors, but this does not provide any new information. A time series image sequence may be viewed repeatedly to obtain a sense of the thermal signal shape over time. This is time consuming and subjective. In the present invention, feature extraction procedures as described above provide two or more parameters, including a signal amplitude parameter and at least one signal shape parameter. The following method is described to simultaneously display two or more parameters in one image.

Thermal signal parameters may be assigned to selected parameters in the so-called HSL color space (Hue, Saturation, Luminance), for example in the following way:
  Hue ⇔ Signal shape aspect 1
  Saturation ⇔ Signal shape aspect 2
  Luminance ⇔ Signal amplitude aspect The term "hue" means color. In the above mapping, the hue of a pixel represents a level of a first thermal signal shape aspect, the saturation represents a level of a second signal shape aspect, and the brightness or luminance represents a level of a signal amplitude aspect. These signal aspects are derived from the time series via curve fitting as described above. Thus, each pixel in a single combined display represents data for a corresponding unit area over a time period. The amplitude aspect for each pixel may represent for example the maximum of the curve, the mean value of the curve over the time period, or the area under the curve integrated over the time period.

If only two parameters are obtained, such as an amplitude aspect and a shape aspect, then the following assignments may be used in one embodiment:
  Hue ⇔ Signal shape aspect
  Saturation ⇔ 100%
  Luminance ⇔ Signal amplitude aspect In the above mapping, the hue of a pixel represents a shape aspect, the brightness or luminance of the pixel represents an amplitude aspect, and the saturation may be fixed at any desired level, such as 100%.

Figure 6:
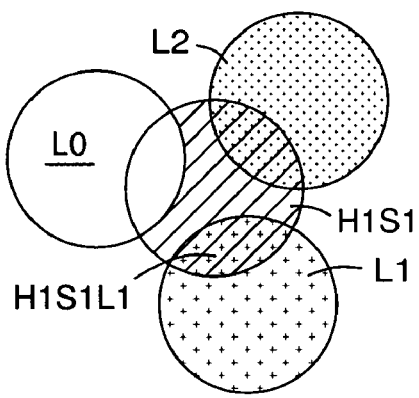
FIG. 6 a Venn diagram illustrating hue, saturation, and luminance overlays.
Figure 7:
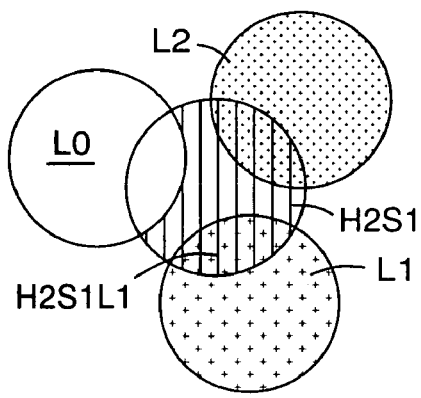
FIG. 7 a Venn diagram as in FIG. 6 with a second hue.
Figure 8:
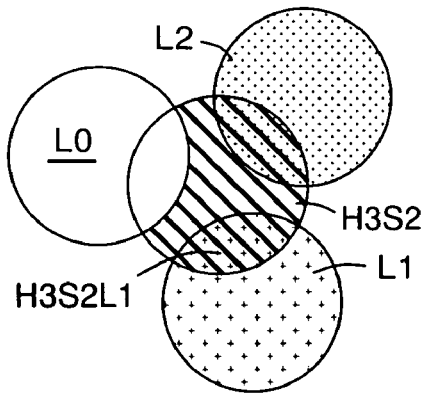
FIG. 8 a Venn diagram as in FIG. 6 with a second saturation level.

FIGS. 6-8 conceptually illustrate with Venn diagrams how hue, saturation, and luminance may be combined in a pixel to represent a plurality of thermal signal parameters. Circles L0, L1, and L2 represent luminance levels of zero, higher, and highest respectively. The central circles of the figures represent hue by hatch direction, and saturation by hatch line thickness. Thus, circle H1S1 of FIG. 6 represents a first hue at a first saturation level. Circle H2S1 of FIG. 7 represents a second hue at the same first saturation level. Circle H3S2 of FIG. 8 represents a third hue at a second saturation level. The intersection areas represent various example combinations of hue, saturation, and luminance as shown. H1S1L1 represents hue 1, saturation 1, and luminance 1. H2S1L1 represents hue 2, saturation 1, and luminance 1. H3S2L1 represents hue 3, saturation 2, and luminance 1. Such combinations display both the amplitude and shape aspects over time in a single image, greatly reducing the time needed for visual analysis, and making it more objective. Note that the intersection of zero luminance with anything is null. This eliminates noise from the combined image as later described.

Figure 9:
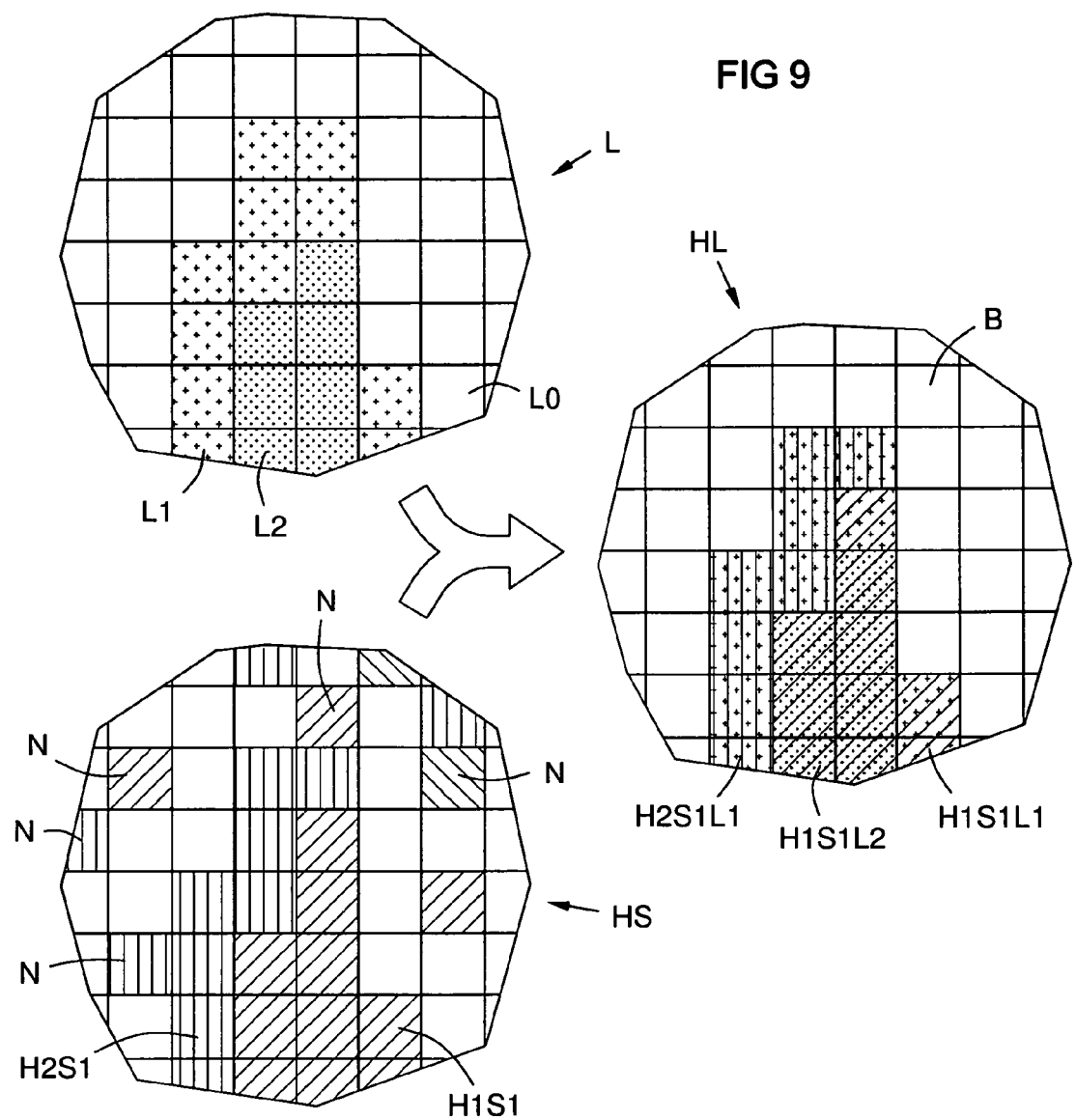
FIG. 9 overlaying luminance and hue arrays to produce a pseudo-color image that displays two aspects of a time series of radiometric images in a single image.

FIG. 9 illustrates two grey-scale images separately representing amplitude and shape aspects being combined in a pseudo-color image representing both aspects. Image L illustrates a grey-scale pixel set representing an amplitude aspect. Image HS illustrates a grey-scale pixel set representing a shape aspect. In this example, only one shape aspect is presented, so the saturation is fixed. The grey scales are symbolized by hatching as in FIGS. 6-8. While the amplitude image L just shows heat sources, the shape image H provides additional information. The shape image H tends to be noisy at the lowest amplitudes because here the shape of the signals is not clearly defined. Wherever the amplitude aspect is so low as to produce a noisy shape aspect, the corresponding luminance pixel may be defined as zero in image L. An amplitude threshold may be set to distinguish between significant and insignificant shape aspects. Some noise pixels N are shown in image H. Images H and L are combined to produce a final pseudo-color display image HL that shows in HSL color space the information from both the L and H images without the individual drawbacks. The image HL is noise free, since the noise pixels are nullified into background pixels B by the intersection with zero luminance pixels. Combined information pixels H2S1L1, H1S1L2, and H1S1L1 are shown. Defects in the part being analyzed now stand out clearly in image HL, and different types of defects and other effects such as lateral heat diffusion can be distinguished by differences in the signal shape-presented in HL by hue. The third value of the HSL space, the saturation, can similarly be used to show a third parameter in the images.

Figure 10:
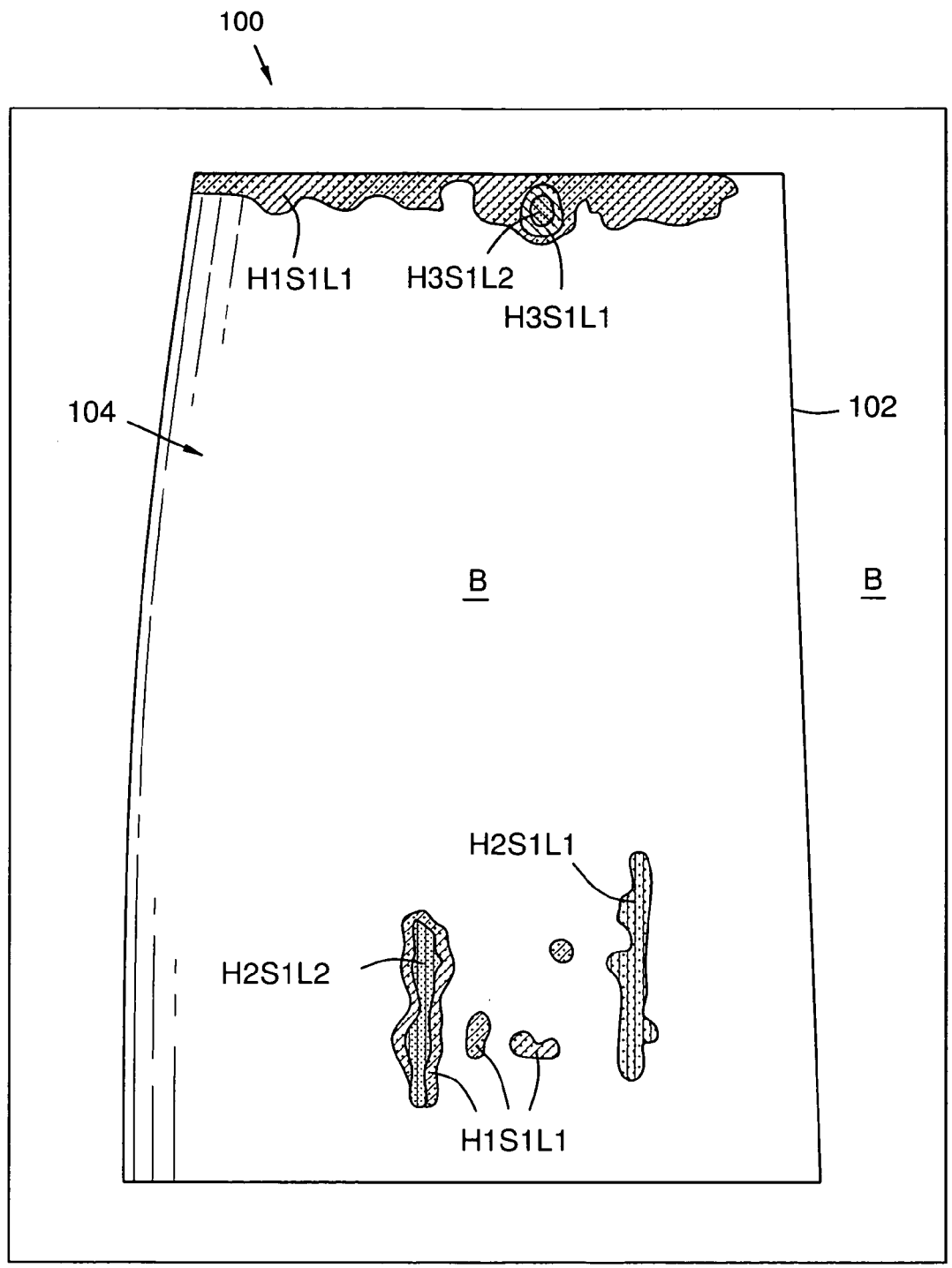
FIG. 10 a thermographic image produced as in FIG. 9 overlaid on a background visible image of the object being analyzed—a turbine blade airfoil in this illustration.

FIG. 10 illustrates a color combination image 100 produced as in FIG. 9 for an array of curves generated for respective plurality of unit areas on an airfoil surface 104 of a gas turbine blade 102 being tested. The image is overlaid on a visible background image of the blade. The background image occupies pixels B in which the amplitude aspect is below the significance threshold. Here the contours of the test sample can clearly be recognized. Some example combined information areas H1S1L1, H2S1L1, H2S1L2, and H3S1L1 are shown. Features and defects can now be seen in the context of blade structure for a determination of restoration or replacement actions needed.

When a component 102 is energized during a thermography examination, the time/temperature data for points/pixels on the surface 104 reflect the relative location of a defect. A single pixel may display an identical time/temperature history for two different defects, such as one defect being located at the surface a distance from the surface pixel and another being located subsurface at a distance below the surface pixel. However, other pixels contiguous (nearby or adjacent) to the single pixel will not exhibit the identical time/temperature history, and thus will reflect a different shape aspect. Thus, the analysis of examination data to identify potential defects in a component necessarily involves the evaluation of not just a single pixel, but also surrounding pixels. The display 100 of FIG. 10 facilitates such multi-pixel time-history analysis by providing a user-friendly manner of presenting both amplitude and shape information. Beneficially, this provides a mechanism for estimating defect depth and/or for deciding if a given feature should be interpreted as a defect or as an artifact of a remotely located defect.

Various methods for processing thermography signals incorporating the present invention may include the steps of collecting a time series of radiometric data for a unit area on a surface of an object over a time period comprising a thermographic energizing phase and a subsequent non-energizing phase; extracting amplitude and shape information from the data such as by fitting a mathematical curve to the time series or otherwise developing parameters representative of amplitude and shape of the time series; and using such information to characterize a feature of the object, such as to diagnose the presence of a flaw in the object. The amplitude and shape information may be presented in HSL color space via a display for viewing by an operator. The shape information may utilize features of the energizing and non-energizing phases of the inspection.

While various embodiments of the present invention have been shown and described herein, it will be obvious that such embodiments are provided by way of example only. Numerous variations, changes and substitutions may be made without departing from the invention herein. For example, the data analysis and information presentation aspects of the present invention may be embodied in non-destructive testing techniques other than thermography; for example x-ray tomography, nuclear magnetic resonance (NMR), ultrasonic testing, eddy current testing, microwave testing, material analysis with microscopy, machine vision, etc. Accordingly, it is intended that the invention be limited only by the spirit and scope of the appended claims.

The invention claimed is:

1. A method for processing thermography signals comprising:
   using a computer/processor to perform the following steps:
   collecting a time series of radiometric data for a unit area on a surface of an object over a time period comprising a thermographic energizing phase and a subsequent non-energizing phase;
   fitting a mathematical curve to the time series;
   identifying an amplitude aspect of the curve;
   identifying a first shape aspect of the curve;
   identifying a second shape aspect of the curve;
   using both the amplitude and shape aspects to characterize a feature of the object; and
   presenting the amplitude aspect, the first shape aspect and the second shape aspect in a picture element using a hue, saturation, luminance (HSL) color space.

2. The method of claim 1 wherein the amplitude aspect of the curve is selected from the group consisting of a maximum of the curve, a mean value of the curve over the time period, and an area under the curve integrated over the time period.

3. The method of claim 1, wherein the first shape aspect of the curve is derived from at least one calculation selected from the group consisting of: an average slope of the curve during the energizing phase; an average slope of the curve during the non-energizing phase; a time associated with a delay of a curve maximum with respect to an energizing cutoff time; a center of gravity of the area integrated under the curve over the time period; a ratio of an area under the curve before a maximum of the curve to an area under the curve after the maximum of the curve; a ratio of an area under the curve during the energizing phase to an area under the curve during the non-energizing phase; a time period defined by a length of a line drawn between the energizing phase and the non-energizing phase at a specified amplitude; a ratio of the time period above a predetermined amplitude during the energizing phase and the time period above that same predetermined amplitude during the non-energizing phase; and a ratio of the curve maximum and a length of a line drawn between the energizing phase and the non-energizing phase at a specified amplitude.

4. The method of claim 1 wherein the mathematical curve is fit to the time series using a type of function selected from the group consisting of linear functions, exponential functions, polynomial functions, error functions, Fourier series, Hermite polynomials, Laguerre functions, spherical Bessel functions, and Legendre polynomials.

5. The method of claim 4 wherein the first shape aspect comprises a type of function selected to have a best fit to the time series.

6. A method for processing thermography signals, comprising:
   receiving a time series of data elements over an array corresponding to a surface of an object being tested, each data element representing a thermal signal from a unit area on the surface;
   fitting a mathematical curve to the data in each data element over the time series;
   identifying an amplitude aspect for each curve;
   identifying a shape aspect for each curve;
   combining the amplitude and shape aspects of each curve in an array of pixels using a hue, saturation, luminance (HSL) color space to create a display; and
   overlaying a visible image of the surface to the display.

7. The method of claim 6, wherein the shape aspect comprises a type of function selected to have a best fit to the time series.

8. The method of claim 6, wherein the shape aspect of the curve is derived from at least one calculation selected from the group consisting of: an average slope of the curve during the energizing phase; an average slope of the curve during the non-energizing phase; a time associated with a delay of a curve maximum with respect to an energizing cutoff time; a center of gravity of the area integrated under the curve over the time period; a ratio of an area under the curve before a maximum of the curve to an area under the curve after the maximum of the curve; a ratio of an area under the curve during the energizing phase to an area under the curve during the non-energizing phase; a time period defined by a length of a line drawn between the energizing phase and the non-energizing phase at a specified amplitude; a ratio of the time period above a predetermined amplitude during the energizing phase and the time period above that same predetermined amplitude during the non-energizing phase; and a ratio of the curve maximum and a length of a line drawn between the energizing phase and the non-energizing phase at a specified amplitude.

9. A method for processing nondestructive testing signals comprising:
   using a computer/processor to perform the following steps:
   identifying an amplitude aspect and first and second shape aspects of a time series of inspection data for a unit area of an object being inspected;

presenting the amplitude aspect and the first and second shape aspects concurrently in a display in a picture element using a hue, saturation, luminance (HSL) color space.

10. The method of claim 9, further comprising overlaying the displayed picture element with a visible image of the object being inspected.

11. The method of claim 9, wherein the nondestructive testing signals comprise thermography signals, and further comprising:

fitting a mathematical curve to a time series of the inspection data;

identifying the amplitude and the first and second shape aspects from the mathematical curve; and combining the amplitude and the first and second shape aspects using a hue, saturation, luminance (HSL) color space to create a display.

12. The method of claim 9, further comprising:

performing the identifying and presenting steps for inspection data for a plurality of contiguous unit areas of the object; and using the display to analyze a feature of the object.

\* \* \* \* \*